United States Patent [19]
Edmunds et al.

[11] Patent Number: 5,966,018
[45] Date of Patent: Oct. 12, 1999

[54] APPARATUS FOR MEASURING VARIATIONS IN THICKNESS OF ELONGATED SAMPLES OF THIN PLASTIC FILM

[76] Inventors: Kevin D. Edmunds; Neil A. Sticha, both of 303 21st St., Suite 221, Newport, Minn. 55055

[21] Appl. No.: 09/024,955

[22] Filed: Feb. 11, 1998

Related U.S. Application Data

[60] Provisional application No. 60/037,614, Feb. 12, 1997.

[51] Int. Cl.⁶ .......................... G01N 27/22; G01R 27/26
[52] U.S. Cl. ........................ 324/663; 324/671; 324/690
[58] Field of Search ................................ 324/661, 662, 324/663, 671, 672, 673, 679, 680, 686, 688, 690

[56] References Cited

U.S. PATENT DOCUMENTS

| | | | |
|---|---|---|---|
| 3,471,780 | 10/1969 | Beddows | 324/671 |
| 3,764,899 | 10/1973 | Peterson et al. | 324/671 |
| 4,952,882 | 8/1990 | Mayer et al. | 324/671 |
| 5,101,166 | 3/1992 | Oestreich et al. | 324/671 |
| 5,793,217 | 8/1998 | Herbst, Jr. | 324/690 |

*Primary Examiner*—Diep Do

[57] ABSTRACT

A capacitance gauge for measuring changes in the thickness of dielectric film, such as plastic film, is automatically temperature and humidity compensated by utilizing a primary measurement sensor and a reference sensor which monitors changes in perceived capacitance caused by ambient temperature and humidity changes or other environmentally induced interferences. The reference sensor counterbalances in an equal an opposite fashion, and thereby automatically cancels, any imbalance in the primary sensor caused by temperature, humidity, or other, fluctuations. An improved film transport assembly for serially examining plastic film material which eliminates errors in thickness measurement location and eliminates variation in distance between individual sensor readings, while at the same time allowing the user of the invention to select from a full variable range of distances between individual sensor readings and also allows accurate positioning of the film in the sensor.

26 Claims, 3 Drawing Sheets

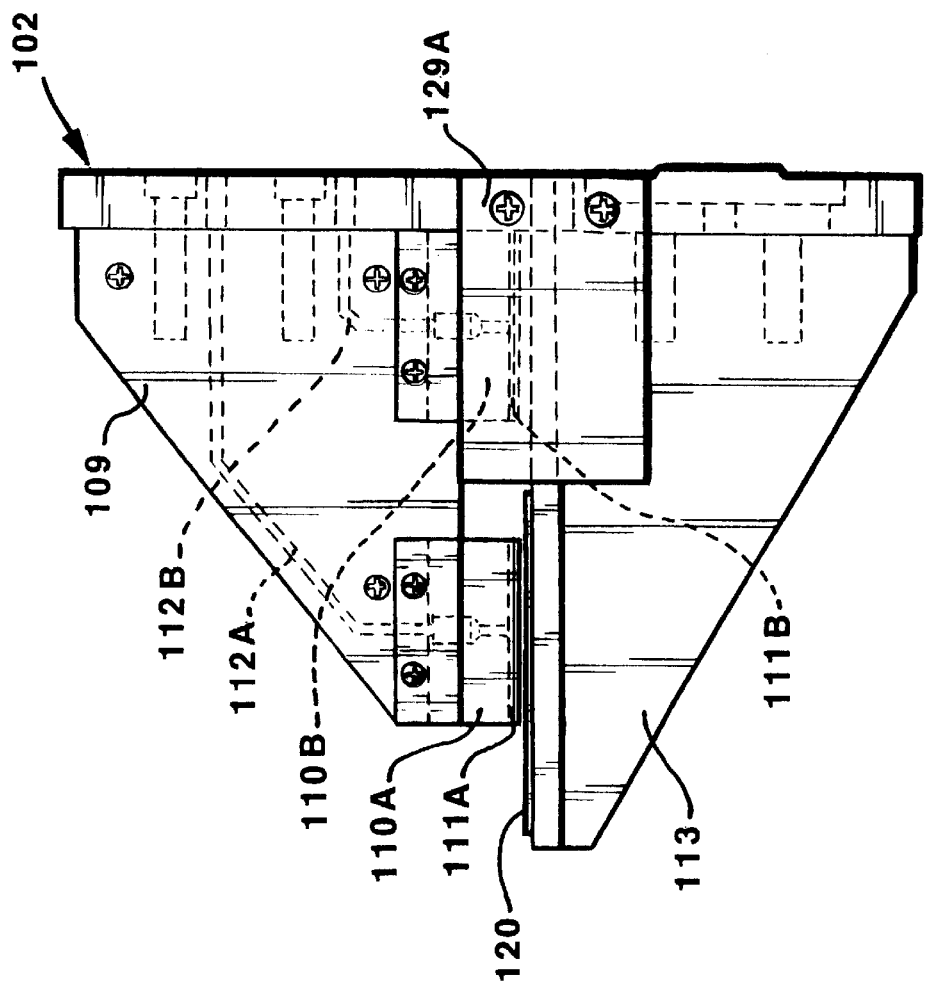
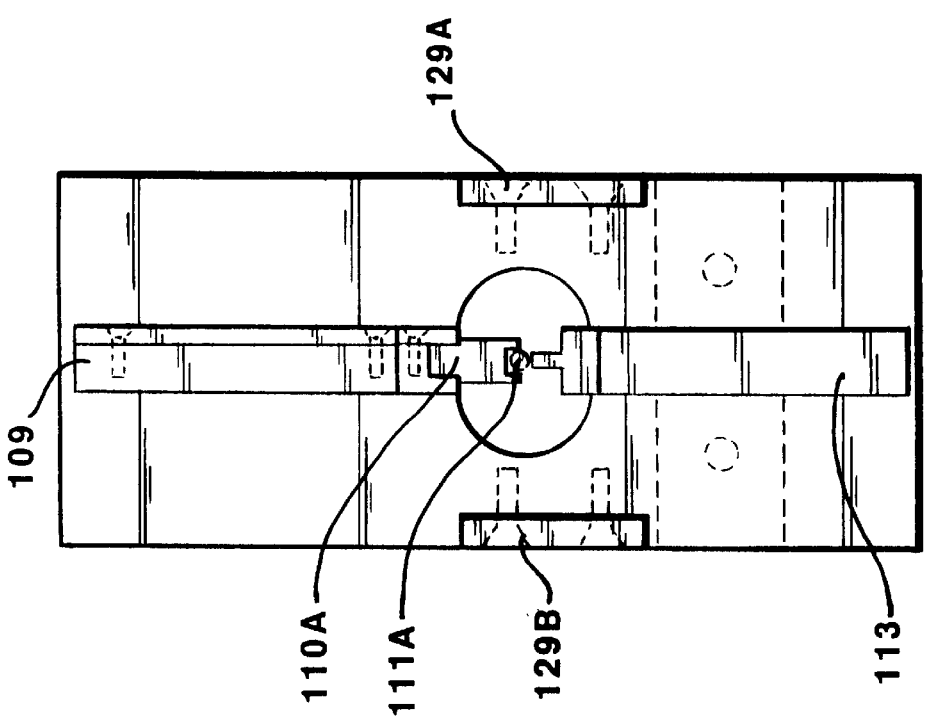

APPARATUS FOR MEASURING VARIATIONS IN THICKNESS OF ELONGATED SAMPLES OF THIN PLASTIC FILM

This application claims benefit of provisional application 60/037,614, filed Feb. 12, 1997.

TECHNICAL FIELD OF THE INVENTION

This invention relates generally to capacitance measuring systems and apparatus for capacitively determining the thickness of dielectric material, such as plastic film. The present invention relates to a capacitive-type thickness measurement apparatus capable of measuring minute variations in the thickness of thin plastic films.

BACKGROUND ART

In the field with which our invention is concerned, the use of capacitive measuring systems for measuring film thickness is known in the art.

One form known in the art is disclosed in U.S. Pat. No. 3,764,899, issued Oct. 9, 1973. This patent measures film thickness by passing the film through a capacitance sensor, wherein variations in film thickness are sensed as dielectric thickness variations between the capacitance members, and are detected as variations in a signal which is applied to the capacitance members. The dimensions and configuration of the "electrodes" or capacitor plates claimed improved characterization of variations in thickness. The patent further claimed a transport for serially examining film material which eliminates errors resulting from tension on the film sample.

Another form of capacitance measuring device is disclosed in U.S. Pat. No. 4,952,882, issued Aug. 28, 1990, which was submitted as an improvement in the construction of the capacitance sensor disclosed in the foregoing United States patent. This capacitance sensor assembly also measures changes in thickness of a dielectric film, such as plastic film, where the sensor components are constructed from materials having low coefficients of linear temperature expansion, resulting in a claimed measurement device which provides low measurement errors resulting from temperature effects on material expansion and dielectric changes. The design concept was to minimize, not eliminate, the errors caused by temperature effects on the sensor assembly.

Another form of capacitance measuring device is disclosed in U.S. Pat. No. 3,471,780, issued Oct. 7, 1969. This capacitance sensor assembly also measures changes in thickness of a dielectric film, such as plastic film, where the sensor design was a single capacitive cell with three capacitor plates, which utilized materials of construction and component dimensions which were claimed to minimize the effects of temperature variations and their related changes in dimensional and dielectric properties of the cell. Moisture effects were claimed to be negated by manually adjusting a micrometer which would move the secondary capacitive plate (center plate of three plates) in the cell to counterbalance the effects of moisture in the atmosphere or film sample. However, there was no allowance to monitor the effects of environmental changes (alone) nor an automatic method to eliminate them from the thickness readings.

SUMMARY OF THE INVENTION

The present invention is an improvement in the construction of the capacitive sensor and related transport for serially examining plastic film material.

Measurement instruments of the type for which the invention finds utility are typically used to measure plastic film thicknesses in the range of 0.001–0.050 inch. Measurement accuracy, of both the film thickness and of thickness measurement locations, should be maintained over a range of ambient temperatures and relative humidities which are found in the typical environment where such instruments are used. A problem in prior art measurement devices has been the inability to maintain accurate measurements of film thickness and thickness measurement location over a range of ambient temperature and humidity changes.

It is therefore an object of our invention to provide an improved capacitance sensor assembly which maintains measurement accuracy over a range of ambient temperatures and humidities by utilizing a primary measurement sensor and a (second) reference sensor which monitors changes in perceived capacitance caused by ambient temperature and humidity changes or other environmentally induced interferences. Capacitance changes due to ambient environment changes which are monitored by the reference sensor are eliminated from the primary sensor readings providing measurement accuracy over said change in ambient environment conditions. Our invention accomplishes this, automatically, without the requirement of utilizing exotic materials in sensor component construction as was required in the prior art.

Another object of our invention is to provide an improved film transport assembly for serially examining plastic film material which eliminates errors in thickness measurement location and eliminates variation in distance between individual sensor readings, while at the same time allowing the user of the invention to select from a full variable range of distances between individual sensor readings (film transport speeds), and also allows accurate positioning of the film in the sensor. The invention utilizes a variable-speed, servo-controlled motor, position feedback device and motor controller assembly to accomplish these improvements.

DESCRIPTION OF THE DRAWINGS

FIG. 2 is an enlarged front elevation of the capacitance sensor assembly shown as a fragmentary portion of FIG. 1;

FIG. 3 is an enlarged side elevation of the capacitance sensor assembly shown as a fragmentary portion of FIG. 1.

DESCRIPTION OF PREFERRED EMBODIMENT

Figure 1:
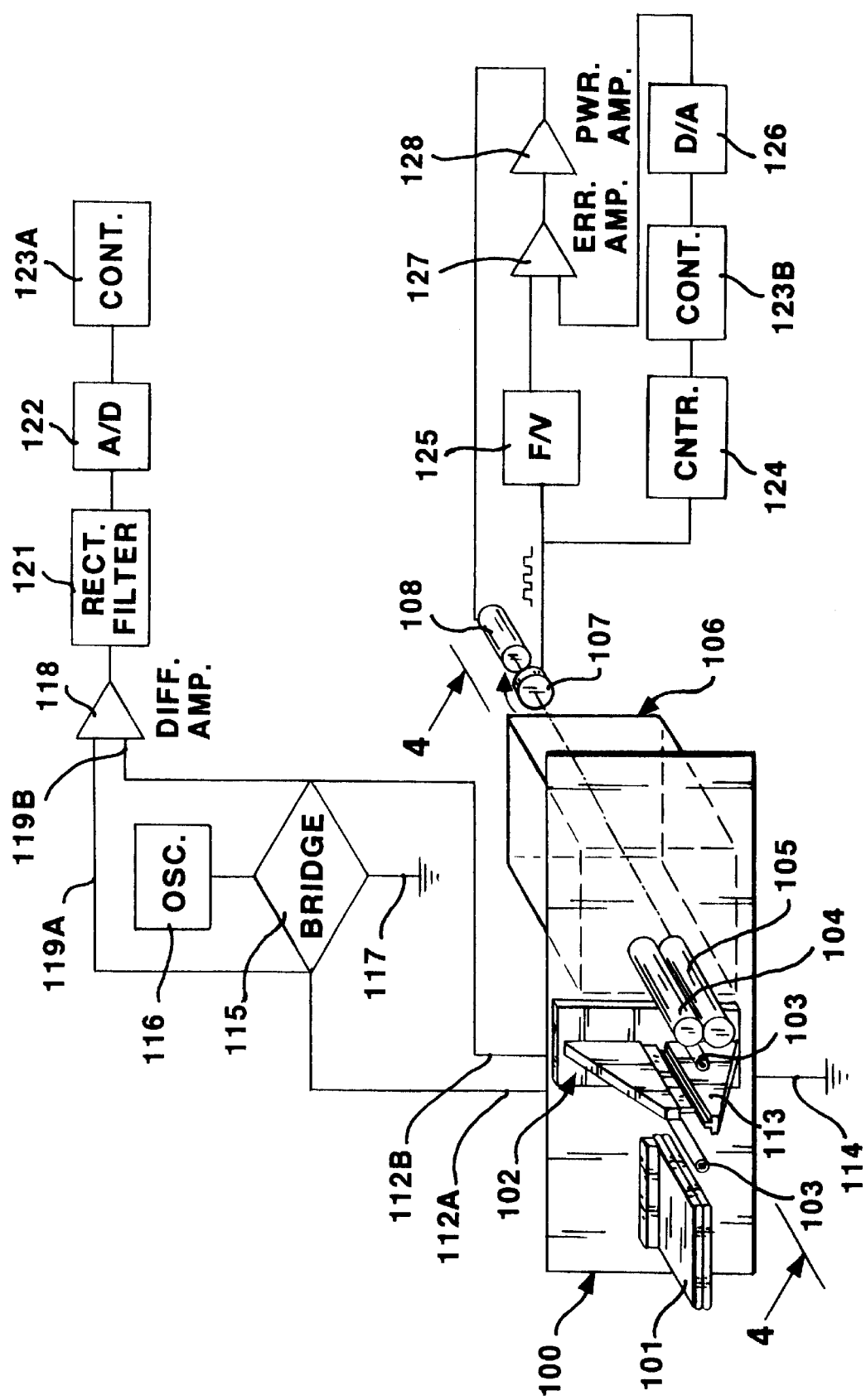
FIG. 1 is a functional schematic diagram of apparatus embodying the principles of our invention.

Referring now to the drawings, the pictorial diagramatic representation in FIG. 1 includes a panel 100 upon which various elements of the system may conveniently be mounted, although, only substantially the mechanical portions are shown in pictorial illustration. Panel 100 forms a support for the forwardly extending film support plate 101, electrode assembly 102, guide bars 103, adjustable idle roller 104, drive roller 105, and forms a support for the backwardly extending film transport carriage 106, drive roller position feedback device 107, and drive motor 108.

While not shown in the drawings, an elongated strip, or web of plastic material is passed over the top of film support plate 101, intermediate guide bars 103, through the electrode assembly 102 and intermediate rollers 104 and 105.

As shown in the enlarged FIGS. 2 and 3 of the drawings, electrode assembly 102 is comprised of a top portion 109 which is adapted to receive and hold two insulated inserts 110A and 110B which, in turn, are each provided with a groove at its lower portion that is adapted to receive and hold two longitudinally elongated electrodes 111A and 111B of subtantially circular cross section. A suitable conductor 112A and 112B is shown connected to each electrode. Another electrode, which may be vertically adjustable upon panel 100, is comprised of current conducting material and is indicated by reference character 113. The other electrode, 113, is provided with a longitudinally elongated raised portion at its center that is adapted to be vertically adjustably disposed in parallel with and substantially underneath electrodes 111A and 111B so as to define, therebetween, a generally uniform gap for slidably receiving the elongated film of dielectric or plastic material, the thickness and variations thereof of which is to be determined. The film material 120 is only allowed to pass under the front of two electrodes, and is prevented from passing under the second reference electrode by standoffs 129A and 129B mounted to the sensor assembly.

Figure 4:
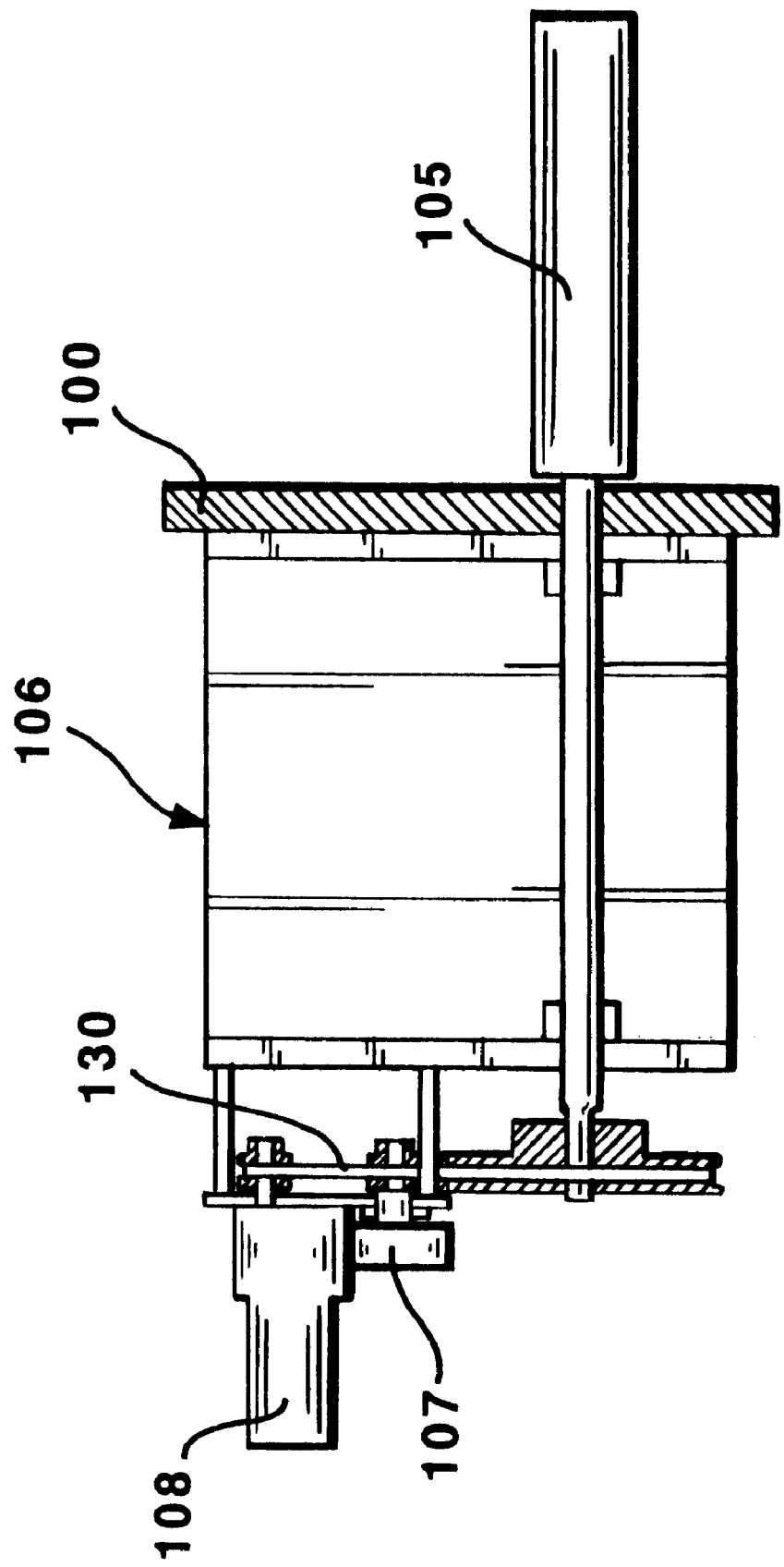
FIG. 4 is a sectional, side elevation of the film transport assembly shown as a fragmentary portion of FIG. 1 taken along line 4—4 of FIG. 1.

As shown in enlarged FIG. 4 of the drawings, the film transport assembly is comprised of film transport carriage 106, which is mounted on panel 100, and is arranged to support drive roller 105, drive roller position feedback device 107, and drive motor 108. In the specific form illustrated, the drive roller 105, drive roller position feedback device 107, and drive motor 108 are connected and driven by a common drive belt 130.

Referring again to FIG. 1, one of the electrodes 113 of electrode assembly 102 is shown connected to ground through conductor 114. The other two longitudinally elongated electrodes are shown having conductors 112A and 112B connected to bridge circuit 115. An oscillator 116 is shown connected to bridge circuit 115 which provides excitation for the bridge, and the remaining bridge terminal is connected to ground through conductor 117. The two side terminals of bridge circuit 115 are connected to differential amplifier 118 through conductors 119A and 119B.

With a single sensing electrode there would be an imbalance in the bridge circuit as a result of the gap closing or opening due to temperature, humidity or environmental fluctuations. Placing a second reference electrode on the other side of the bridge circuitry will counterbalance in an equal and opposite fashion, and thereby cancel, any imbalance in the sensing electrode caused by temperature, humidity or environmental fluctuations.

The differential amplifier 118 amplifies any difference between the front sensing electrode and the second reference electrode caused by the addition of the film sample 120 between the front sensing electrodes. The amplified output is rectified & filtered in the rectifier/filter circuit 121 to convert the alternating current difference signal to a direct current signal, and is then converted from an analog signal to a digital signal in the A/D converter 122 and is then sent to the microcontroller 123A for data collection and analysis.

Referring again to FIG. 1, output pulses from the drive roller position feedback device 107 are counted by counter 124 to monitor position travelled, and are also sent to the frequency-to-voltage converter 125. From counter 124 the position information is transmitted to the microcontroller 123B.

Setpoint speed information is entered into the microcontroller 123B by the operator, and is converted by the digital-to-analog converter 126 and sent to the input side of error amplifier 127, where it is compared to the actual speed signal from the frequency to voltage converter 125. The error amplifier 127 sends a signal to the power amplifier 128 which increases or decreases voltage to the drive motor 108 until set point speed equals actual speed. The system continually monitors and maintains correct drive motor speed.

The components utilized in the system disclosed as an illustrative embodiment of our invention may readily be determined by those skilled in the art.

The present invention may be embodied in other specific forms without departing from the spirit or essential attributes thereof, and it is therefore desired that the present embodiment be considered in all respects as illustrative and not restrictive.

We claim:

1. A capacitance electrode assembly adapted for attachment to a mounting plate for measuring changes in thickness of a dielectric film comprising:
   a) a back plate;
   b) means for connecting the back plate to the mounting plate;
   c) a primary sensor assembly and a reference sensor assembly;
   d) means for connecting the primary and reference sensor assembly to the back plate;
   e) each sensor assembly having;
      1) a lower housing connected to the back plate having an elongated upper portion projected away from the back plate;
      2) an elongated first electrode extended along said upper portion of the lower housing;
      3) an upper housing connected to the back plate having an elongated lower portion located in substantial vertical alignment with said elongated first electrode;
      4) electrical insulator means mounted on the elongated lower portion of the upper housing; and
      5) said primary sensor assembly having a second electrode mounted on the electrical insulator means, said reference sensor assembly having a third electrode mounted on the electrical insulator means, said second and third electrodes being axially spaced from each other and spaced from the first electrode;
   f) guide means for preventing the film from passing between the first electrode and third electrode and allowing the film to pass between the first electrode and second electrode;
   g) a bridge circuit electrically coupled to the second and third electrodes whereby the reference sensor assembly counterbalances the bridge circuit and cancels any imbalance in the primary sensor assembly caused by temperature, humidity or other fluctuations; and
   h) means for moving the film between the first and second electrodes.

2. The electrode assembly of claim 1 including: means for vertically adjusting the lower housing on said back plate.

3. The electrode assembly of claim 1 wherein: the second and third electrodes are linear members having substantially the same lengths.

4. The electrode assembly of claim 3 wherein: the linear members are cylindrical electrical conductors.

5. The electrode assembly of claim 3 wherein: the linear members are axially aligned and have adjacent spaced ends.

6. The electrode assembly of claim 1 wherein: the guide means comprise a pair of plates connected to the back plate adjacent opposite sides of the upper and lower housings.

7. The electrode assembly of claim 1 wherein: the means for moving the film between the first and second electrodes comprises a film transport assembly for serially examining the thickness of the film.

8. The electrode assembly of claim 7 wherein: the film transport assembly comprises rollers for moving the film, an amplifier and variable speed motor assembly to drive the rollers for advancing the film between the first and second electrodes, a position feed back device to monitor motor speed and position of the rollers, and a controller to monitor and maintain the speed of the motor and stop and start the motor to position the film relative to the first and second electrodes.

9. A capacitance electrode assembly for measuring changes in thickness of a dielectric film comprising:
   a) a primary sensor assembly;
   b) a reference sensor assembly;
   c) said primary and reference sensor assembly having;
      1) a first housing having an elongated first portion;
      2) an elongated first electrode located along said portion of the first housing;
      3) a second housing having an elongated second portion located in substantial vertical alignment with said first electrode and extended substantially parallel to said first electrode;
      4) electrical insulator means mounted on the elongated second portion of the second housing; and
      5) said primary sensor assembly having a second electrode mounted on the electrical insulator means, said reference sensor having a third electrode mounted on the electrical insulator means, said second and third electrodes being laterally spaced from each other and spaced from the first electrode;
   d) guide means for preventing the film from passing between the first and third electrodes and allowing the film to pass between the first and second electrodes;
   e) means electrically coupled to the second and third electrodes whereby the reference sensor assembly cancels imbalances in the primary sensor assembly caused by temperature, humidity or other fluctuations; and
   f) means for moving the film between the first and second electrodes.

10. The electrodes assembly of claim 9 including: means for adjusting the location of the first and second housing relative to each other to adjust the space between the first electrode and the second and third electrodes.

11. The electrode assembly of claim 9 wherein: the second and third electrodes are linear electrode members having substantially the same lengths.

12. The electrode assembly of claim 11 wherein: the linear electrode members are cylindrical electrical conductors.

13. The electrode assembly of claim 11 wherein: the linear electrode members are axially aligned and have adjacent spaced ends.

14. The electrode assembly of claim 9 wherein: the guide means comprise at least one member for preventing the film from passing between the first electrode and the third electrode.

15. The electrode assembly of claim 9 wherein: the means for moving the film between the first and second electrodes comprises a film transport assembly for serially examining the thickness of the film.

16. The electrode assembly of claim 15 wherein: the film transport assembly comprises rollers for moving the film, an amplifier and variable speed motor assembly to drive the rollers for advancing the film between the first and second electrodes, a position feed back device to monitor motor speed and position of the rollers, and a controller to monitor and maintain the speed of the motor and stop and start the motor to position the film relative to the first and second electrodes.

17. The capacitance electrode assembly of claim 9 wherein: the means electrically coupled to the second and third electrodes includes a bridge circuit that is counterbalanced by the reference sensor assembly and cancels any imbalances in the primary sensor assembly caused by temperature, humidity or other fluctuations.

18. A capacitance electrode assembly for measuring changes in thickness of a dielectric film comprising:
   a) a first electrode;
   b) a second electrode;
   c) a third electrode;
   d) said second and third electrodes being linearly aligned with each other and laterally spaced from each other and aligned with and spaced from the first electrode;
   e) guide means for preventing the film from passing between the first and third electrodes and allowing the film to pass between the first and second electrodes;
   f) means electrically coupled to the second and third electrodes to cancel imbalances in the electrical signals sensed between the first and second electrodes with electrical signals sensed between the first and third electrodes caused by temperature, humidity or other fluctuations; and
   g) means for moving the film between the first and second electrodes.

19. The electrodes assembly of claim 18 including: means for adjusting the locations of the second and third electrodes relative to the first electrode to adjust the space between the first electrode and the second and third electrodes.

20. The electrode assembly of claim 18 wherein: the second and third electrodes are linear members having substantially the same lengths.

21. The electrode assembly of claim 20 wherein: the linear members are cylindrical electrical conductors.

22. The electrode assembly of claim 20 wherein: the linear members are axially aligned and have adjacent spaced ends.

23. The electrode assembly of claim 1 wherein: the guide means comprise a pair of plates for preventing the film from passing between the first electrode and third electrode.

24. The electrode assembly of claim 7 wherein: the means for moving the film between the first and second electrodes comprises a film transport assembly for serially examining the thickness of the film.

25. The electrode assembly of claim 24 wherein: the film transport assembly comprises rollers for moving the film, an amplifier and variable speed motor assembly to drive the rollers for advancing the film between the first and second electrodes, a position feed back device to monitor motor speed and position of the rollers, and a controller to monitor and maintain the speed of the motor and stop and start the motor to position the film relative to the first and second electrodes.

26. The electrode assembly of claim 18 wherein: the means electrically coupled to the second and third electrodes includes a bridge circuit that is counterbalanced by the electrical signals sensed between the first and second electrodes with electrical signals sensed between the first and third electrodes caused by temperature, humidity or other fluctuations.

* * * * *